(12) United States Patent
Tapp

(10) Patent No.: US 11,964,123 B2
(45) Date of Patent: Apr. 23, 2024

(54) TOOL FOR ENGAGING AND DISENGAGING CONNECTORS

(71) Applicant: 0411261 BC Ltd., Abbotsford (CA)

(72) Inventor: Michael Robert John Tapp, Abbotsford (CA)

(73) Assignee: 0411261 BC Ltd., Abbotsford (CA)

( * ) Notice: Subject to any disclaimer, the term of this patent is extended or adjusted under 35 U.S.C. 154(b) by 445 days.

(21) Appl. No.: 17/321,804

(22) Filed: May 17, 2021

(65) Prior Publication Data

US 2022/0362539 A1 Nov. 17, 2022

(51) Int. Cl.
*A61M 39/10* (2006.01)
*A61M 39/12* (2006.01)

(52) U.S. Cl.
CPC .... *A61M 39/1011* (2013.01); *A61M 39/1055* (2013.01); *A61M 39/12* (2013.01)

(58) Field of Classification Search
CPC ..... B25B 13/5091; B25B 13/48; B25B 13/02; B25B 13/04; B25F 1/00; A61M 39/1011; A61M 39/1055; A61M 39/12
USPC ................................. D8/21, 17, 19
See application file for complete search history.

(56) References Cited

U.S. PATENT DOCUMENTS

| | | | | |
|---|---|---|---|---|
| D120,489 S | * | 5/1940 | Musselman | 81/124.4 |
| D130,756 S | * | 12/1941 | Howard | 7/138 |
| D268,473 S | * | 4/1983 | Rust | D8/17 |
| D288,893 S | * | 3/1987 | Epstein | D8/19 |
| 4,685,360 A | * | 8/1987 | McCurdy | B25B 13/02 |
| | | | | 81/119 |
| D311,313 S | * | 10/1990 | Whiteside | D8/27 |
| 5,425,292 A | * | 6/1995 | Mobile | B25B 13/56 |
| | | | | 81/177.1 |
| D360,117 S | * | 7/1995 | Mobile | D8/17 |
| 5,673,976 A | * | 10/1997 | Hillis | B25B 13/48 |
| | | | | 301/58 |
| D417,372 S | * | 12/1999 | Cachot | D8/21 |
| D445,655 S | * | 7/2001 | Maddox | D8/19 |
| D473,766 S | * | 4/2003 | Williams | D8/21 |
| 7,024,968 B2 | * | 4/2006 | Raudabough | A61M 5/347 |
| | | | | 81/124.2 |
| 7,117,766 B1 | * | 10/2006 | Boehringer | B25B 13/5091 |
| | | | | 81/125 |
| 7,926,392 B2 | * | 4/2011 | Thompson | F16D 65/0043 |
| | | | | 81/119 |
| 8,826,776 B2 | * | 9/2014 | Junk | B25F 1/00 |
| | | | | 7/138 |
| 9,452,511 B2 | * | 9/2016 | Nguyen | B25B 13/48 |

(Continued)

*Primary Examiner* — David B. Thomas
(74) *Attorney, Agent, or Firm* — McDonnell Boehnen Hulbert & Berghoff LLP

(57) ABSTRACT

A tool for engaging and disengaging connectors. The tool includes a longitudinal member and at least one aperture extending through the member. The aperture is sized and shaped to receive and retain a connector, and is configured to rotate the connector to engage and disengage the connector with a mating connector. In some of the embodiments a pair of such tools are utilized, one tool holding a first connector and a second tool holding a second connector. In these embodiments one tool may be held stationary while the other tool is rotated to engage and disengage the connectors as desired. Alternatively, both tools may be simultaneously rotated in opposite directions engage and disengage the connectors as desired.

2 Claims, 8 Drawing Sheets

(56) References Cited

U.S. PATENT DOCUMENTS

| | | | |
|---|---|---|---|
| 9,631,889 B2* | 4/2017 | Geissele | B25B 13/50 |
| 9,784,520 B2* | 10/2017 | Geissele | F41A 11/00 |
| D803,020 S * | 11/2017 | Cheng | D8/21 |
| D805,865 S * | 12/2017 | Sui | D8/21 |
| 9,857,138 B2* | 1/2018 | Geissele | B25B 13/48 |
| 10,063,025 B2* | 8/2018 | Small | B25B 13/04 |
| 10,112,293 B2* | 10/2018 | Cheng | B25B 15/008 |
| 10,406,342 B2* | 9/2019 | Ueda | A61M 39/1011 |
| 2006/0130617 A1* | 6/2006 | Mamourian | A61M 39/1055 81/119 |
| 2018/0085610 A1* | 3/2018 | Aroonsawat | B25B 13/5091 |

\* cited by examiner

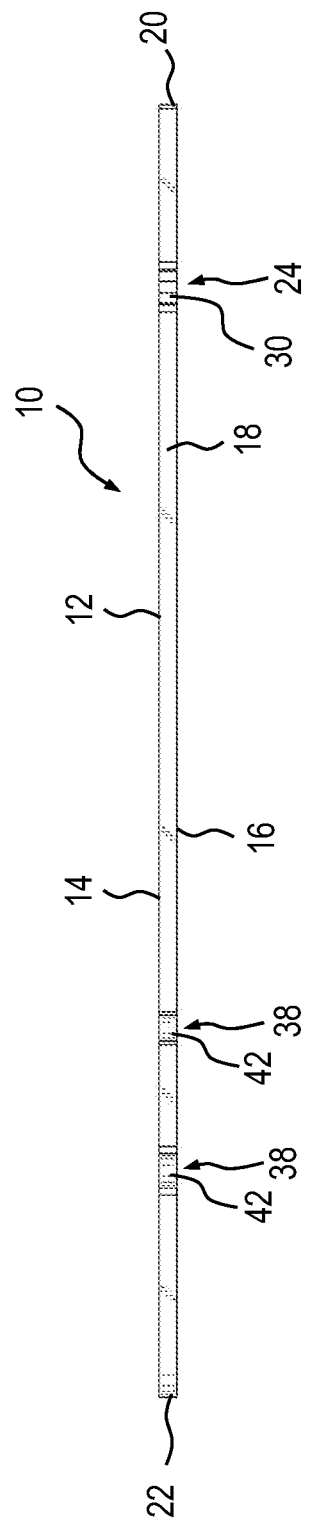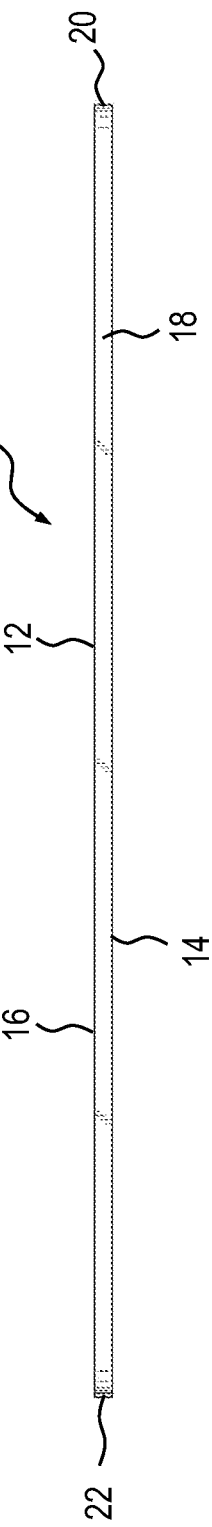

TOOL FOR ENGAGING AND DISENGAGING CONNECTORS

FIELD

The present invention relates generally to tube fittings, connectors, extension lines, caps, and other medical grade equipment used in intravenous therapy.

BACKGROUND

Equipment used for intravenous therapy usually includes a catheter inserted into a vein of a patient and connected to a sterile dispensing container via tubing. In addition to the tubing, intravenous therapy equipment includes various connecting devices such as, without limitation, needle-free caps, extension lines, flushing caps and syringe caps, hereafter referred to generally as "connectors." As one example, BD brand intravenous lines and associated products incorporate such connectors. A pair of connectors are typically engaged or disengaged by placing mating features of the connectors in contact with one another and rotating one of the connectors to engage and disengage them. Alternatively, both connectors may be simultaneously rotated in opposite directions, i.e., clockwise and counter-clockwise, to engage and disengage them.

Medical personnel and patients usually engage and disengage the connectors by hand. To prevent leakage or contamination of fluids from an intravenous system it is necessary to securely couple the connectors together. However, a drawback of these intravenous connecting devices is that they can be difficult to tighten when being engaged. Furthermore, once engaged, the connectors can be difficult to loosen and disengage from one another by hand. This is particularly the case for medical personnel and patients with challenges such as arthritis, limited hand movement, loss of strength, and fatigue. There is a need for a way for persons with such limitations to easily engage and disengage intravenous connectors.

SUMMARY

A tool to engage and disengage intravenous connectors is disclosed. The tool includes a longitudinal member and at least one aperture extending through the member. The aperture is sized and shaped to receive and retain a connector. In some embodiments of the present invention a plurality of apertures may be formed in the tool, the apertures each being sized and shaped to receive and retain a certain type of connector. Such a "multi-tool" can be configured to rotationally engage or disengage a variety of types of connectors.

The disclosed invention describes a tool for engaging and disengaging connectors. The tool includes a longitudinal member and at least one aperture extending through the member. The aperture is sized and shaped to receive and retain a connector. The tool is rotated to rotate a select connector to engage and disengage the connector with a mating connector. The at least one aperture may be a number of sizes and shapes and include a number of types of engagement features, as detailed below.

In an embodiment of the present invention a user holds a connector in one hand while using the tool with the other hand to rotate a mating connector to either engage or disengage the connectors as desired. Alternatively, a pair of said tools may be used, each connector being retained by a corresponding tool. One tool, holding a first connector, may be kept relatively stationary while the other tool is rotated to engage or disengage a second connector with the first connector as desired. Alternatively, both tools may be simultaneously rotated in opposite directions, i.e., clockwise and counter-clockwise, to engage or disengage the connectors as desired.

BRIEF DESCRIPTION OF THE DRAWINGS

Further features of the present invention will become apparent to those skilled in the art to which the present invention relates from reading the following specification with reference to the accompanying drawings, in which:

FIG. 2 is a first elevational side view of the tool of FIG. 1;

FIG. 3 is a second, opposing elevational side view of the tool of FIG. 1;

DETAILED DESCRIPTION

Figure 1:
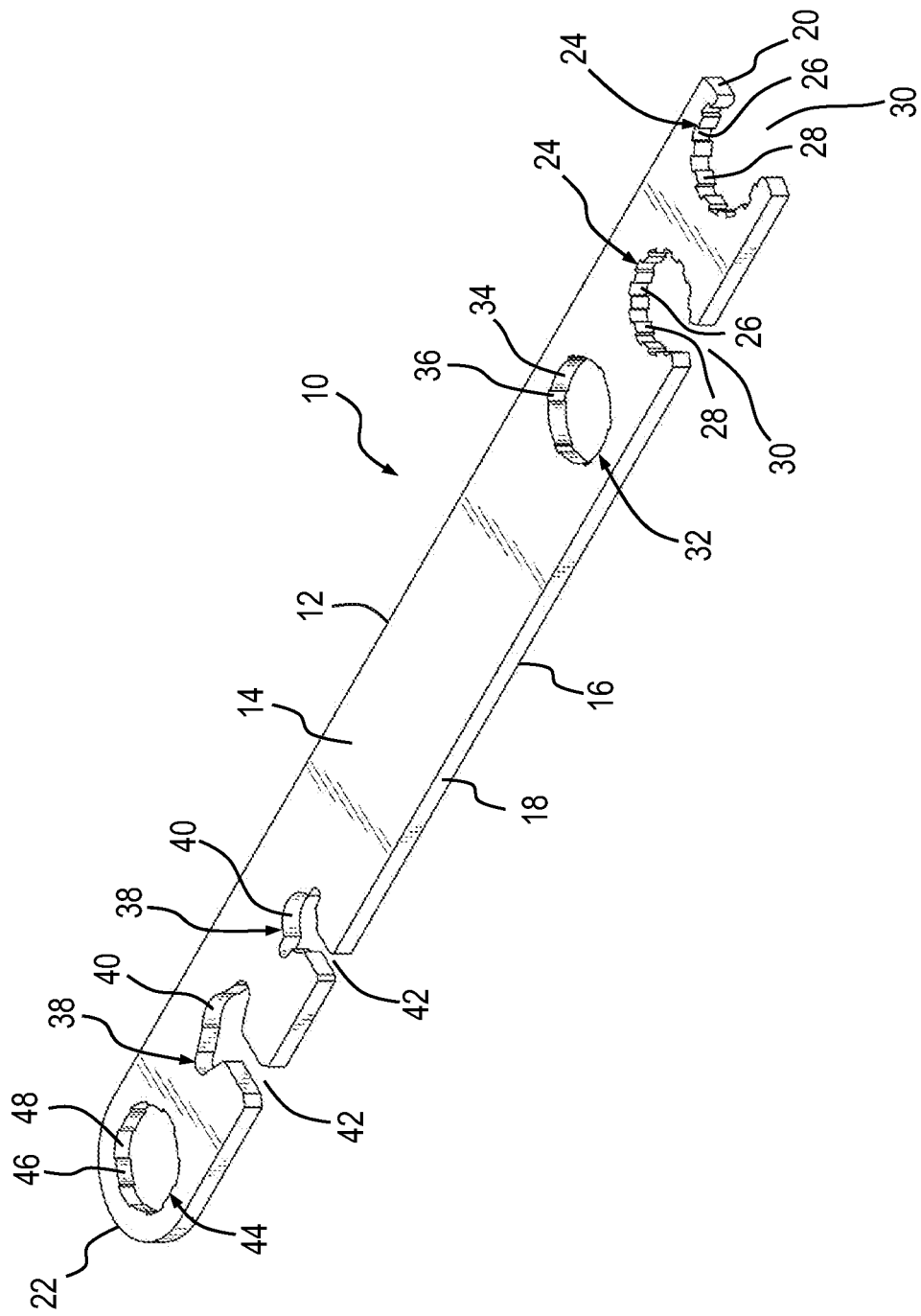
FIG. 1 is a perspective view of a tool for engaging and disengaging connectors according to an embodiment of the present invention.
Figure 4:
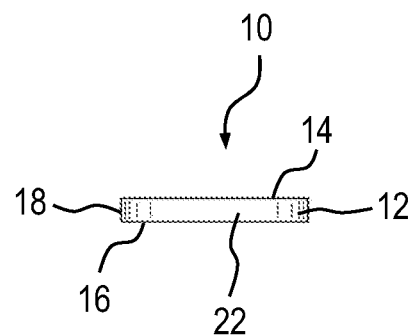
FIG. 4 is a first elevational end view of the tool of FIG. 1.
Figure 5:
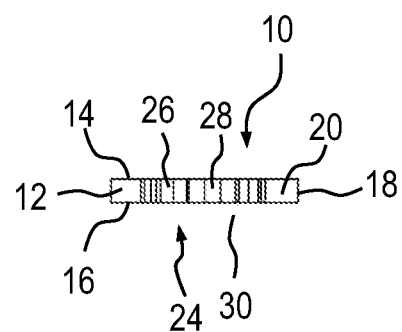
FIG. 5 is a second, opposing elevational end view of the tool of FIG. 1.

The general arrangement of a tool 10 for engaging or disengaging connectors is shown in FIGS. 1 through 7 according to an embodiment of the present invention. Tool 10 includes a generally planar member 12 having a first side 14, a second, opposing side 16, an edge 18 extending between the first and second sides, a first distal end 20 and a second distal end 22.

As further shown in the figures, tool 10 preferably includes one or more apertures extending through member 12, the apertures being sized and shaped to receive and retain a not-shown connector. The types of apertures may vary in size, shape and features to accommodate a particular connector, as discussed further below.

Referring to FIGS. 1, 2, 5, 6 and 7, a first type of aperture 24 extends through first and second sides 14, 16 of member 12. Aperture 24 includes a sidewall 26 extending between the first and second sides 14, 16 and a plurality of spaced-apart, tooth-like projections 28 extending away from the sidewall. The size and shape of aperture 24 as well as the number, size, shape, spacing and locations of tooth-like projections 28 are selected to receive and engage a connector having a corresponding size and complementary features. Aperture 24 may extend to edge 18 as shown and form a gap 30. Alternatively, aperture 24 may be spaced away from edge 18. Two examples of aperture 24 with larger and smaller aperture and gap 30 size to receive and retain a first and a second type of connector respectively are shown in the figures.

Figure 6:
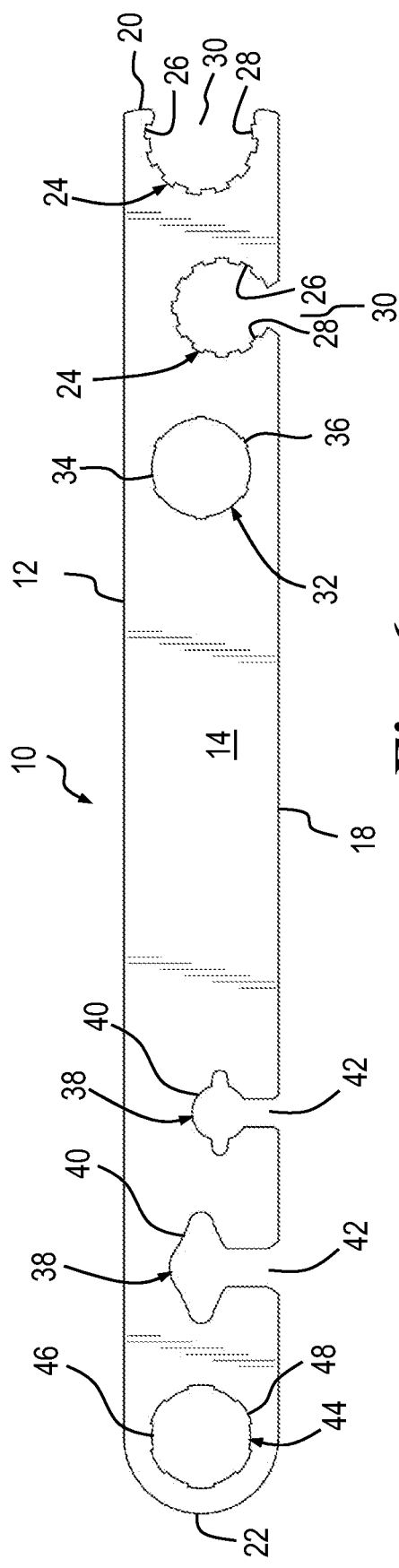
FIG. 6 is a top plan view of the tool of FIG. 1.
Figure 7:
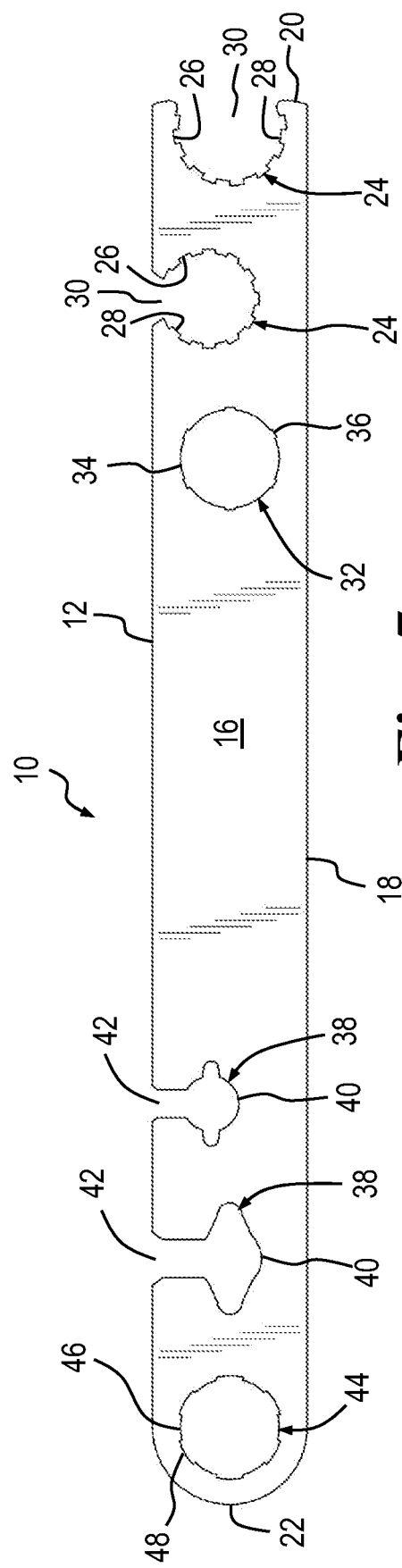
FIG. 7 is a bottom, opposing plan view of the tool of FIG. 1.

A second type of aperture 32 is shown in FIGS. 1, 6 and 7. Aperture 32 extends through first and second sides 14, 16 of member 12. Aperture 32 includes a sidewall 34 extending between the first and second sides 14, 16. Aperture 32 further includes a set of detents 36 extending away from sidewall 34. The size and shape of aperture 32 as well as the number, size, shape, spacing and locations of detents 36 are selected to receive and engage a third type of connector having a corresponding size and complementary features. Aperture 32 may extend to edge 18 in a manner similar to aperture 24, or may be spaced away from the edge as shown.

A third type of aperture 38, shown in FIGS. 1, 2, 6 and 7, extends through first and second sides 14, 16 of member 12. Aperture 38 includes a sidewall 40 extending between the first and second sides 14, 16 and is generally T-shaped. Aperture 38 may extend to edge 18 as shown to form a gap 42, or may be spaced away from the edge.

The size and shape of aperture 38 are selected to receive and engage a connector having a corresponding size and complementary features. For example, aperture 38 may vary in size and "T" shape as desired to receive and retain a corresponding connector. Two examples of aperture 38 of smaller and larger size to receive and retain fourth and fifth types of connectors respectively are shown in the figures.

A fourth type of aperture 44 extends through first and second sides 14, 16 of member 12. Aperture 44 includes a sidewall 46 extending between the first and second sides 14, 16. Aperture 44 further includes a set of detents 48 extending away from sidewall 46. The size and shape of aperture 44 as well as the number, size, shape, spacing and locations of detents 48 are selected to receive and engage a sixth type of connector having a corresponding size and complementary features. Aperture 44 may extend to edge 18 in a manner similar to aperture 24, or may be spaced away from the edge as shown.

Figure 8:
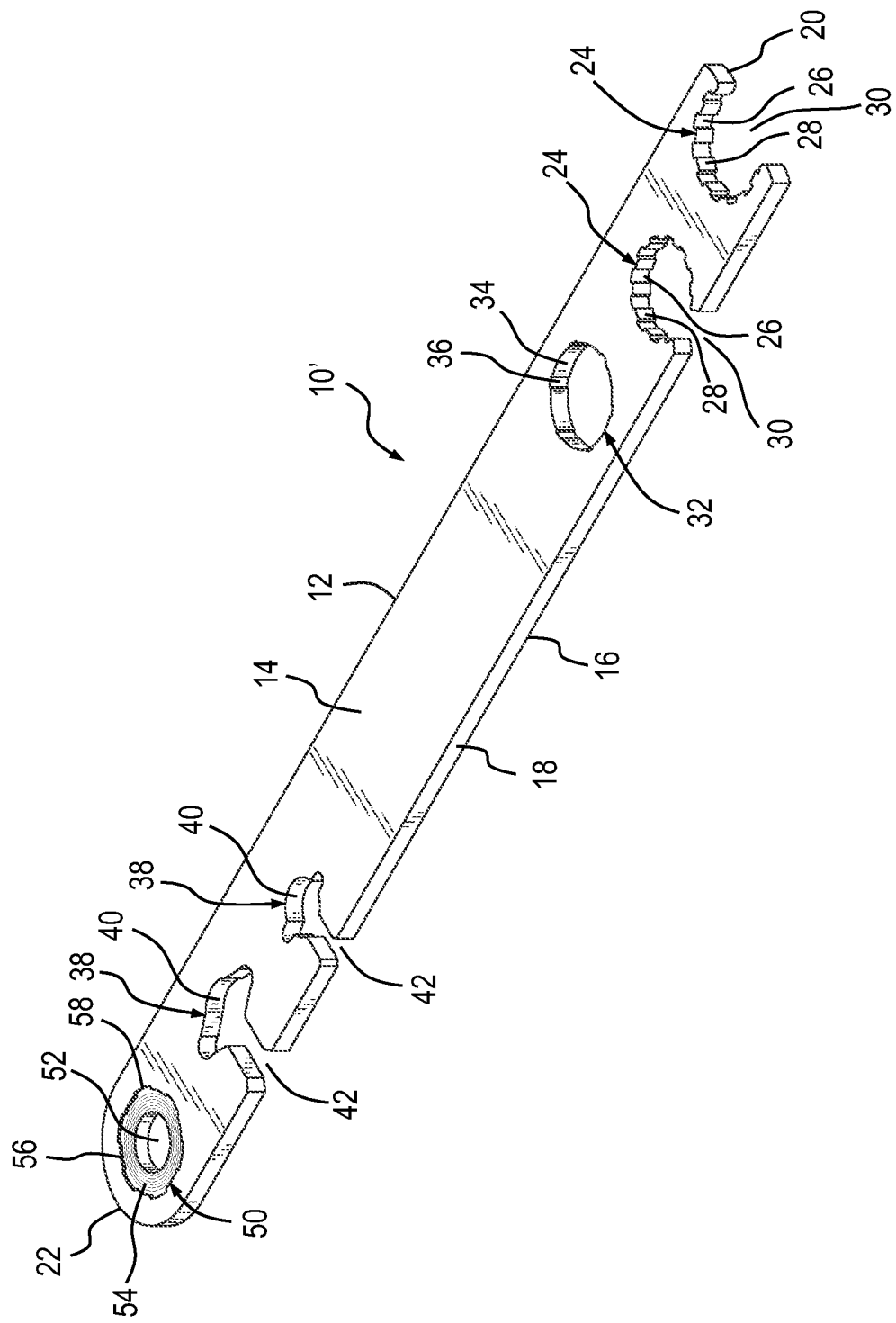
FIG. 8 is a perspective view of a tool for engaging and disengaging connectors according to an alternate embodiment of the present invention.

FIG. 8 shows a tool 10' with a fifth type of aperture 50 according to an alternate embodiment of the present invention. Aperture 50 includes a through hole 52 extending through first and second sides 14, 16 of member 12, a counterbored portion 54 with a sidewall 56 extending between the counterbored portion and front side 14, and a plurality of detents 58 extending away from the sidewall. The size and shape of aperture 50 and through-hole 52 as well as the number, size, shape, spacing and locations of detents 58, and the depth of counterbored portion 54 are selected to receive and engage a connector having a corresponding size and complementary features.

Aperture 50 may extend to edge 18, or may be spaced away from the edge as shown. In some embodiments of the present invention aperture 50 may comprise an opposing counterbore forming a second sidewall and detents similar to sidewall 56 and detents 58.

The various apertures described above may be formed in member 12 in any suitable manner. Examples include, but are not limited to, machining, molding, water-jetting, casting, and stamping. It should also be noted that the present invention is not limited to the apertures described above. Apertures of any size, shape, surfaces, features, and spacings may be formed as needed to receive and retain a connector having a corresponding size and shape within the scope of the invention.

Tool 10 may be made as a generally planar substrate and from any suitable material. Example materials include, without limitation, metals such as medical grade steel, plastic, and composite materials. Tool 10 may further be finished as desired with a finish that is suitable for the select material, such as anodizing, conversion coatings, dyes, pigments, powder coating and paint.

With reference now to FIGS. 1, 6 and 7, in use a single tool 10 may be used to engage and disengage a pair of connectors. A user places a first one of the connectors (not shown) into an appropriate one of the apertures 24, 32, 38, 44, 50 of tool 10 such that the select aperture receives and retains the first connector. The user may then hold tool 10 (and the first connector) in one hand while rotatably engaging or disengaging a second not-shown connector to the first connector with the user's other hand as desired.

With continued reference to FIGS. 1, 6 and 7, a pair of tools 10 may also be used to join or uncouple a pair of connectors. A user places a first one of the connectors into an appropriate one of the apertures 24, 32, 38, 44, 50 of a first tool 10 such that the select aperture receives and retains the first connector. Likewise, the user places a second one of the connectors into an appropriate one of the apertures 24, 32, 38, 44, 50 of a second tool 10 such that the select aperture receives and retains the second, mating connector. The user may then hold one of the first or second tools 10 stationary in one hand while rotating the other tool with the other hand to rotatably engage or disengage the first and second connectors as desired. Alternatively, the user may simultaneously rotate both tools 10 in opposite directions, i.e., clockwise and counterclockwise, to engage or disengage the first and second connectors as desired.

Figure 9:
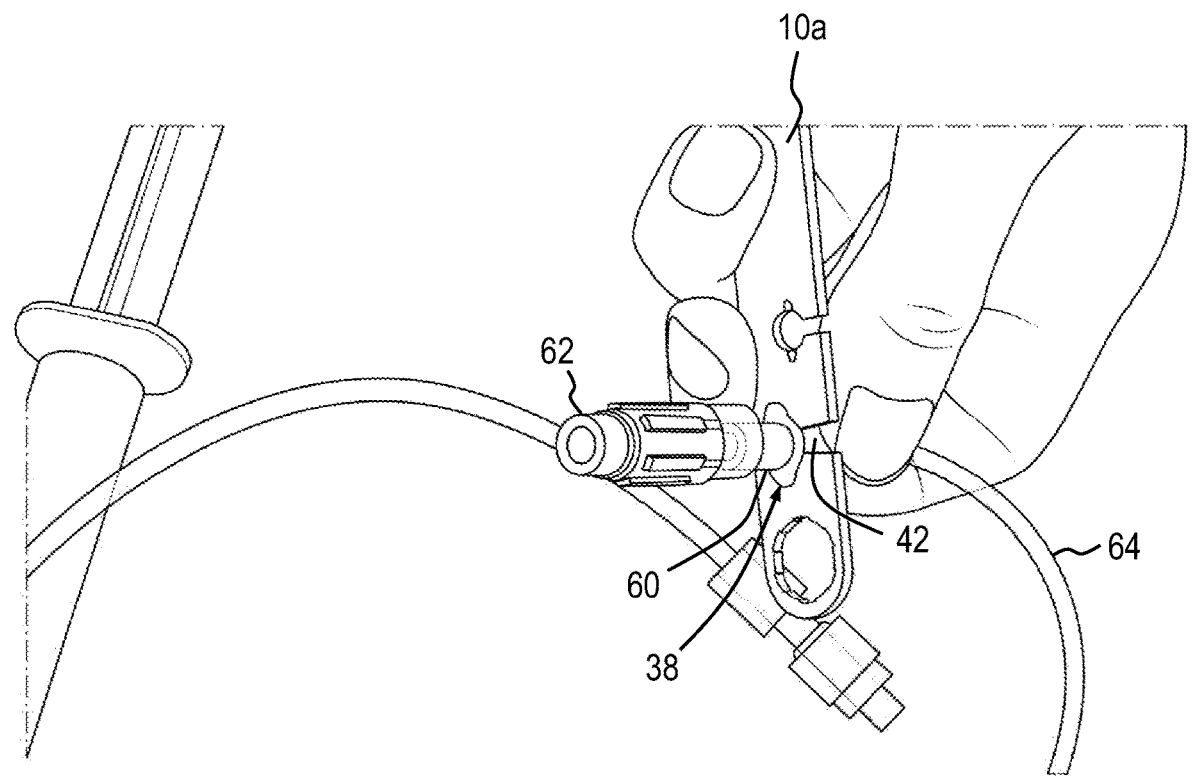
FIG. 9 shows a first connector positioned in a first tool with a second connector attached to the first connector.
Figure 10:
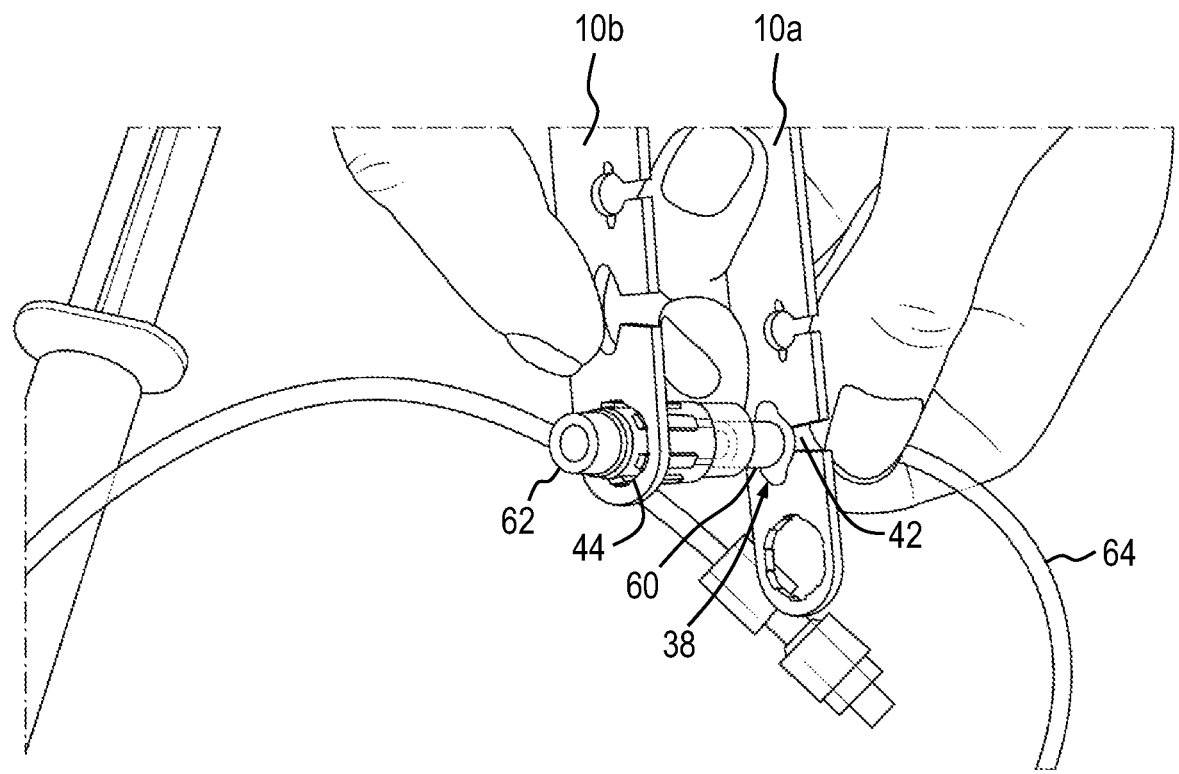
FIG. 10 shows the second connector of FIG. 9 positioned in a second tool.
Figure 11:
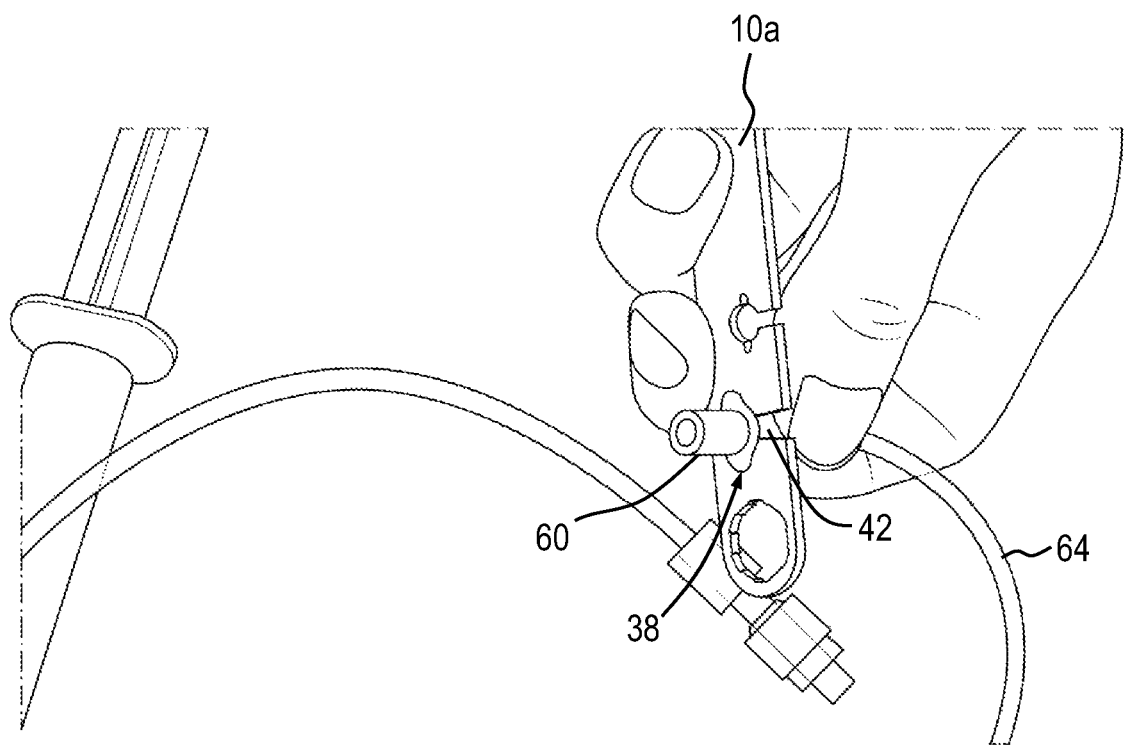
FIG. 11 shows the first connector and first tool of FIG. 9 with the second connector removed.

An example use of tool 10 is shown in FIGS. 9, 10 and 11 for further illustration. A first connector 60 is inserted into an aperture 38 of a first tool 10a (FIG. 9). An aperture 44 of a second tool, 10b, is positioned to engage a second connector 62 that is coupled to first connector 60 (FIG. 10). Either or both of tools 10a, 10b are then rotated as needed to loosen or tighten the engagement of connectors 60, 62. When loosening the connectors 60, 62 the connectors may also be disengaged and detached from one another (FIGS. 10, 11).

Gap 42 may be used to pass an intravenous line 64 (FIGS. 9, 10, 11) into and out of tool 10a. Any of gaps 30, 42 shown in the figures may likewise be used for this purpose when placing a connector into tool 10 or removing a connector from the tool.

From the above description of the invention, those skilled in the art will perceive improvements, changes, and modifications in the invention. Such improvements, changes, and modifications within the skill of the art are intended to be covered. For example, the tool described herein may be used to advantage with any type of connectors that are rotationally engaged and disengaged, whether or not associated with an intravenous system or other types of connectors.

What is claimed is:

1. A tool for engaging and disengaging connectors, comprising:
    a generally planar, longitudinal member having a first side, a second, opposing side and an edge extending between the first and second sides, a first distal end, and a second, opposing distal end;
    a first aperture formed in the first distal end of the member and configured to receive and retain a first type of connector, the first aperture extending through the first and second sides of the member and further extending to the edge of the member to form a first gap, the first aperture having a first sidewall and a plurality of spaced-apart, tooth-like projections extending away from the first sidewall;
    a second aperture formed in the member, the second aperture extending through the first and second sides of the member, configured to receive and retain a second type of connector, and extending to the edge of the member to form a second gap, the second aperture having a second sidewall and a plurality of spaced-apart, tooth-like projections extending away from the second sidewall;

a third aperture formed in the member, the third aperture extending through the first and second sides of the member, configured to receive and retain a third type of connector, and being spaced away from the edge of the member, the third aperture having a third sidewall and a plurality of detents extending away from the third sidewall;

a fourth, generally T-shaped aperture formed in the member and configured to receive and retain a fourth type of connector, the fourth aperture extending through the first and second sides of the member, the fourth aperture having a fourth sidewall and extending to the edge of the member to form a third gap;

a fifth, generally T-shaped aperture formed in the member and configured to receive and retain a fifth type of connector, the fifth aperture extending through the first and second sides of the member, the fifth aperture having a fifth sidewall, the fifth aperture extending to the edge of the member to form a fourth gap, the fifth aperture being larger than the fourth aperture; and a sixth aperture formed in the member proximate the second distal end of the member and configured to receive and retain a sixth type of connector, the sixth aperture extending through the first and second sides of the member and being spaced away from the edge of the member, the sixth aperture having a sixth sidewall and a plurality of detents extending away from the sixth sidewall, the apertures, detents and tooth-like projections of the apertures being configured receive and retain the connectors, and the tool being configured to rotate the connectors to engage and disengage the connectors with a mating connector.

2. The tool of claim 1 wherein the member is made of metal.

* * * * *